US00PP35740P2

(12) United States Plant Patent
Gomez Bullis

(10) Patent No.: US PP35,740 P2
(45) Date of Patent: Apr. 9, 2024

(54) ***AECHMEA* PLANT NAMED 'BLUE WAVE'**

(50) Latin Name: ***Aechmea fendleri* X *Aechmea dichlamydea var. trinitensis***
Varietal Denomination: Blue Wave

(71) Applicant: BULLIS BROMELIADS INC., Princeton, FL (US)

(72) Inventor: Patricia E. Gomez Bullis, Princeton, FL (US)

(73) Assignee: BULLIS BROMELIADS INC., Princeton, FL (US)

( * ) Notice: Subject to any disclaimer, the term of this patent is extended or adjusted under 35 U.S.C. 154(b) by 0 days.

(21) Appl. No.: 18/220,241

(22) Filed: Jul. 10, 2023

(51) Int. Cl.
*A01H 5/02* (2018.01)
*A01H 6/22* (2018.01)

(52) U.S. Cl.
USPC ..... Plt./370

(58) Field of Classification Search
USPC ..... Plt./263.1, 370
See application file for complete search history.

*Primary Examiner* — Karen M Redden
(74) *Attorney, Agent, or Firm* — C. Anne Whealy

(57) ABSTRACT

A new and distinct cultivar of *Aechmea* plant named 'Blue Wave', characterized by its relatively compact plant habit with upright to outwardly arching growth habit; long linear leaves with pale yellow and green-colored longitudinal stripes; freely-flowering habit with inflorescences held upright and above the foliar plane on strong dark red-colored scapes; long branched inflorescences with dark violet blue-colored flowers, dark violet blue-colored flower bracts and red purple-colored scape bracts; long-lasting inflorescences and good container and interiorscape performance; and resistance to *Pythium* Root Rot.

2 Drawing Sheets

Figure 1:
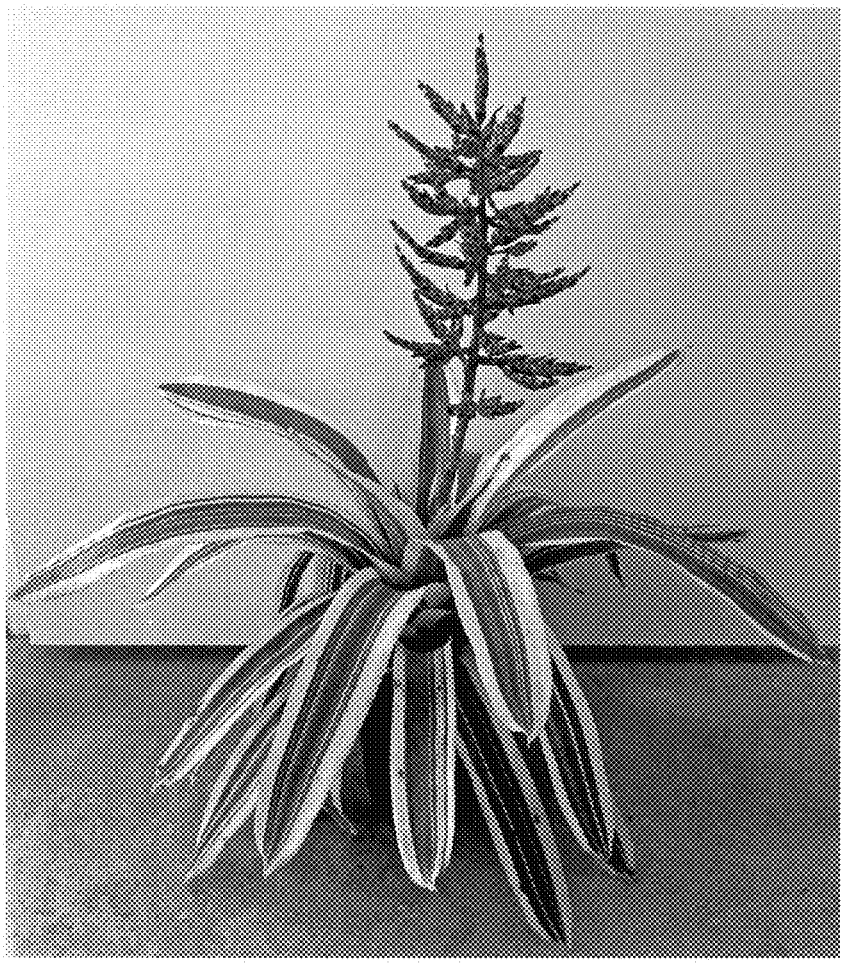

Botanical designation: *Aechmea fendleri* X *Aechmea dichlamydea* var. *trinitensis*.

Cultivar denomination: 'BLUE WAVE'.

BACKGROUND OF THE INVENTION

The present invention relates to a new and distinct *Aechmea* plant, botanically known as *Aechmea fendleri* X *Aechmea dichlamydea* var. *trinitensis* and hereinafter referred to by the cultivar name 'Blue Wave'.

The new *Aechmea* plant is a product of a planned breeding program conducted by the Inventor in Princeton, Florida. The objective of the breeding program was to create new *Aechmea* plants with unique foliage and inflorescence coloration and good postproduction longevity.

The new *Aechmea* plant is a naturally-occurring mutation of *Aechmea fendleri* X *Aechmea dichlamydea* var. *trinitensis* 'Del Mar', disclosed in U.S. Plant Pat. No. 13,421. The new *Aechmea* plant was discovered and selected by the Inventor as an offset of a single flowering plant from within a population of plants of 'Del Mar' in Princeton, Florida in 2016.

Asexual reproduction of the new *Aechmea* plant by offsets in a controlled greenhouse environment in Princeton, Florida since 2016 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Blue Wave'. These characteristics in combination distinguish 'Blue Wave' as a new and distinct *Aechmea* plant:

1. Relatively compact plant habit with upright to outwardly arching growth habit.
2. Long linear leaves with pale yellow and green-colored longitudinal stripes.
3. Freely-flowering habit with inflorescences held upright and above the foliar plane on strong dark red-colored scapes.
4. Long branched inflorescences with dark violet blue-colored flowers, dark violet blue-colored flower bracts and red purple-colored scape bracts.
5. Long-lasting inflorescences and good container and interiorscape performance.
6. Resistant to *Pythium* Root Rot.

Plants of the new *Aechmea* differ primarily from plants of the mutation parent, 'Del Mar' in leaf color as leaves of plants of the new *Aechmea* have pale yellow and green-colored longitudinal stripes whereas plants of 'Del Mar' have solid green-colored leaves.

Plants of the new *Aechmea* can be compared to plants of *Aechmea fendleri* X *Aechmea dichlamydea* var. *trinitensis* 'Del Cielo', disclosed in U.S. Plant Pat. No. 28,922. In side-by-side comparisons, plants of the new *Aechmea* and 'Del Cielo' differ primarily in leaf color as leaves of plants of the new *Aechmea* have pale yellow and green-colored longitudinal stripes with pale yellow-colored margins whereas plants of 'Del Cielo' have creamy white, light green and green variegated leaves with green-colored margins.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color values cited in the detailed botanical description which accurately describe the colors of the new *Aechmea* plant.

The photograph on the first sheet (FIG. 1) is a side perspective view of a typical flowering plant of 'Blue Wave' grown in a container.

Figure 2:
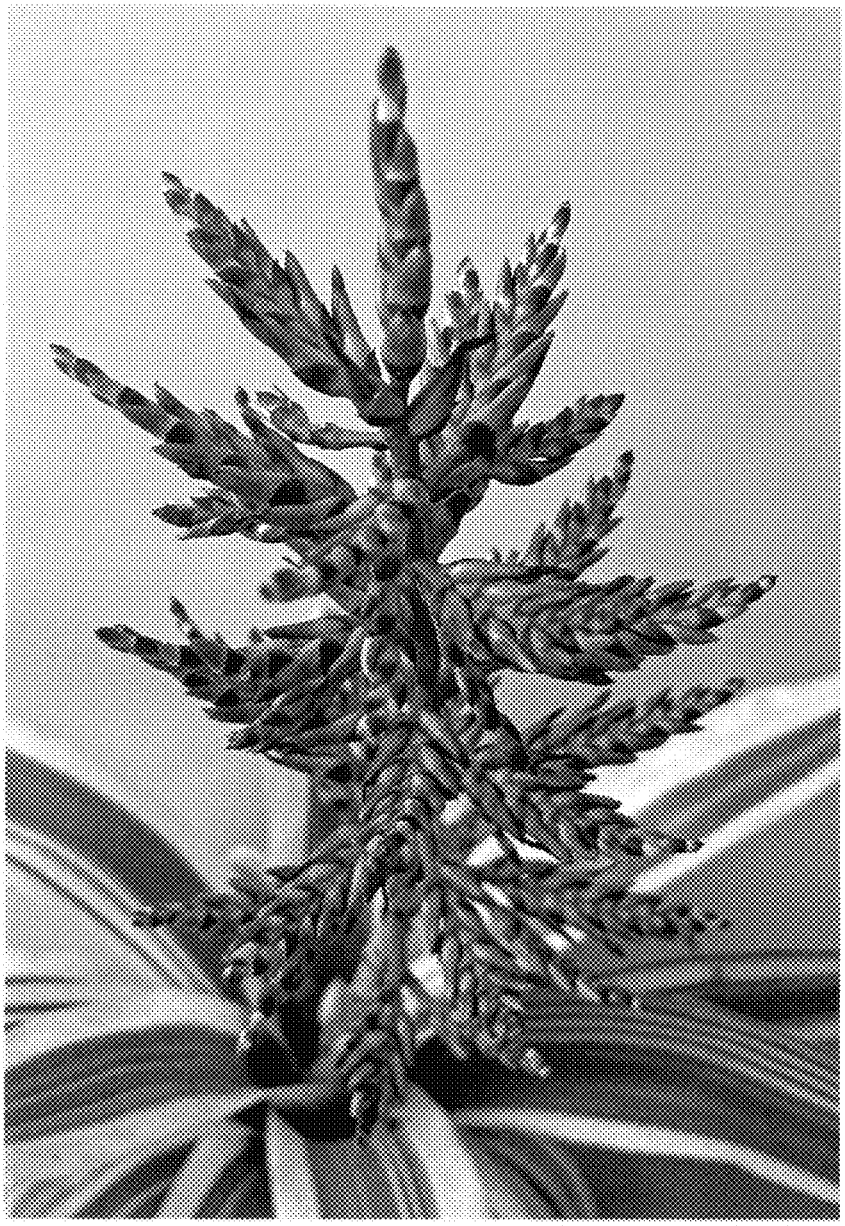

The photograph on the second sheet (FIG. 2) is a close-up view of a typical flowering plant of 'Blue Wave'.

DETAILED BOTANICAL DESCRIPTION

The aforementioned photographs and following observations, measurements and values describe plants grown in 15-cm containers during the spring and early summer in a polypropylene-covered shadehouse in Princeton, Florida. During the production of the plants, day temperatures ranged from 18 C to 27 C, night temperatures ranged from 18 C to 22 C and light levels ranged from 2,200 to 3,200 foot-candles. Plants were 13 months old when the photographs and description were taken. In the following description, color references are made to The Royal Horticultural Society Colour Chart, 2015 Edition, except where general terms of ordinary dictionary significance are used.

Botanical classification: *Aechmea fendleri* X *Aechmea dichlamydea* var. *trinitensis* 'Blue Wave'.

Parentage: Naturally-occurring mutation of *Aechmea fendleri* X *Aechmea dichlamydea* var. *trinitensis* 'Del Mar', disclosed in U.S. Plant Pat. No. 13,421.

Propagation:

*Type*.—By offsets.

*Time to initiate roots, summer*.—About 45 to 60 days at temperatures ranging from 18 C to 27 C.

*Time to initiate roots, winter*.—About 75 to 90 days at temperatures ranging from 18 C to 22 C.

*Time to produce a rooted young plant, summer*.—About 90 days at temperatures ranging from 18 C to 27 C.

*Time to produce a rooted young plant, winter*.—About 120 days at temperatures ranging from 18 C to 22 C.

*Root description*.—Fine, fibrous; typically yellow to beige in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Relatively compact plant habit with upright to outwardly arching growth habit; rosette leaves are mostly erect when young becoming outwardly arching with development; plants readily produce offsets; moderately vigorous growth habit.

*Plant height, soil surface to top of leaf canopy*.—About 35 cm.

*Plant height, soil surface to top of inflorescence*.—About 55 cm.

*Plant diameter or spread*.—About 56 cm to 62 cm.

Leaf description:

*Arrangement*.—Rosette, spiral phyllotaxis; leaves clasping; simple.

*Length*.—About 37 cm.

*Width, flattened*.—About 6.5 cm.

*Shape*.—Linear, strap-like.

*Apex*.—Sharply cuspidate to aristate.

*Base*.—Truncate.

*Margin*.—Pectinate; sharply spinose.

*Aspect*.—Mostly upright to outwardly arching with development.

*Texture and luster, upper surface*.—Smooth, glabrous; leathery; stiff; glossy.

*Texture and luster, lower surface*.—Smooth, glabrous; leathery; stiff; moderately glossy.

*Venation*.—Parallel.

*Color*.—Developing and fully expanded leaves, upper surface: Pale yellow-colored central and marginal longitudinal stripes, close to 150D, 154D and 160C; green-colored central stripes, close to 144A and 146A. Developing and fully expanded leaves, lower surface: Pale yellow-colored central and marginal longitudinal stripes, close to 150D and 160D; green-colored central stripes, close to 144A and 146A.

*Marginal spines*.—Density: About two to three per cm. Length: About 2 mm. Diameter: About 1 mm. Shape: Acicular with sharp apices. Texture and luster: Smooth, glabrous; glossy. Color: Close to 154D; at the apices, close to 187A.

Inflorescence description:

*Inflorescence form and arrangement*.—Open terminal panicles with tightly branched lateral panicles supported by erect and strong scapes; about 22 to 24 primary lateral panicles each with up to two developing secondary lateral panicles; each primary lateral panicle with about 12 to 15 individual flowers; flowers distichous, sessile.

*Time to flower*.—Plants begin flowering about 12 to 15 weeks after planting.

*Inflorescence longevity*.—Inflorescences of the new *Aechmea* are very long-lasting, typically inflorescence color will be maintained for about two to five months in the interior landscape depending on environmental conditions; flowers and inflorescences persistent.

*Fragrance*.—None detected.

*Inflorescence length*.—About 46 cm.

*Inflorescence width*.—About 11 cm to 12 cm.

*Primary lateral inflorescence length*.—About 7 cm.

*Primary lateral inflorescence width*.—About 1.5 cm.

*Secondary lateral inflorescence length* (*developing*).—About 4 cm.

*Secondary lateral inflorescence width* (*developing*).—About 1.25 cm.

*Flower length*.—About 1.6 cm.

*Flower diameter*.—About 5 mm.

*Petals*.—Quantity and arrangement: Three in a single whorl; firmly fused at least 90% of the petal length. Length: About 1.5 cm. Width, proximally: About 4 mm. Shape: Elongated ovate to lanceolate. Apex: Acute. Base: Truncate. Margin: Entire. Texture and luster, inner and outer surfaces: Smooth, glabrous, waxy; glossy. Color: When opening and fully opened, inner surface: Close to 157A. When opening and fully opened, outer surface: Proximally, close to 157A; distally, close to N88A.

*Sepals*.—To date, sepal development has not been observed on plants of the new *Aechmea*.

*Flower bracts*.—Quantity and arrangement: One per flower; subtending and closely appressed to the flower. Length: About 7.5 mm. Width, flattened: About 5 mm. Shape: Broadly ovate. Apex: Cuspidate to aristate. Base: Truncate. Margin: Entire. Texture and luster, upper and lower surfaces: Smooth, glabrous, waxy; somewhat glossy. Color, upper and lower surfaces: Close to N88A and N89A.

*Scape bracts*.—Quantity and arrangement: One subtending each lateral panicle. Length: About 3 cm. Width: About 1.1 cm. Shape: Lanceolate. Apex: Acuminate. Base: Truncate. Margin: Entire. Texture and luster, upper and lower surfaces: Smooth, glabrous; papery; somewhat glossy. Color, upper surface: Close to 59A to 59B; becoming brownish with subsequent development. Color, lower surface: Close to 59A; becoming brownish with subsequent development.

*Scapes*.—Length, primary scape, to base of inflorescence: About 22 cm. Diameter, primary scape: About 1 cm. Length, lateral scapes: About 1.4 cm to 1.6 cm. Diameter, lateral scapes: About 3 mm to 4 mm. Strength, primary and lateral scapes: Strong. Aspect, primary scape: Upright. Aspect, lateral scapes: About 45 to 90 degrees to primary scape axis. Texture and luster, primary and lateral scapes: Smooth, glabrous; slightly glossy. Color, primary scape: Proximally, close to 144B; distally, close to 59A. Color, lateral scapes: Close to 59A.

*Reproductive organs*.—Stamens: Quantity per flower: Six. Filament length: About 4 mm. Filament color: Close to 162A to 162B. Anther length: Less than 1 mm. Anther shape: Oblong. Anther color: Close to 162C. Pollen: None observed. Pistils: Quantity per flower: One. Pistil length: About 1.2 cm. Style length: About 1 cm. Style color: Close to 162A to 162B. Stigma shape: Ovoid. Stigma color: Close to 163A. Ovary color: Close to 157A.

*Seeds*.—To date, seed production has not been observed on plants of the new *Aechmea*.

Temperature tolerance: Plants of the new *Aechmea* have been observed to tolerate temperatures ranging from about 2 C to about 33 C.

Pathogen & pest resistance: Plants of the new *Aechmea* have been observed to exhibit resistance to *Pythium* Root Rot (*Pythium* spp.). Plants of the new *Aechmea* not been observed to be resistant to pests and other pathogens common to *Aechmea* plants.

It is claimed:

1. A new and distinct *Aechmea* plant named 'Blue Wave' as illustrated and described.

* * * * *